United States Patent [19]

Mora

[11] Patent Number: 4,477,458
[45] Date of Patent: Oct. 16, 1984

[54] THIAZOLIDINE DERIVATIVES AND THEIR MUCOLYTIC COMPOSITIONS AND METHODS

[75] Inventor: Camillo C. Mora, Piacenza, Italy

[73] Assignee: Camillo Corvi S.p.A., Italy

[21] Appl. No.: 374,776

[22] Filed: May 4, 1982

[30] Foreign Application Priority Data

May 12, 1981 [IT] Italy ................. 21654 A/81

[51] Int. Cl.³ .................. A61K 31/425; C07D 277/04
[52] U.S. Cl. .................... 424/266; 424/251; 424/270; 544/335; 546/256; 546/280; 548/200
[58] Field of Search ............... 548/200; 546/280, 256; 544/335; 424/251, 266, 270

[56] References Cited

U.S. PATENT DOCUMENTS 4,021,435  5/1977  Cavazza ................. 546/280
4,066,614  1/1978  Oppelt et al. ............ 544/173

FOREIGN PATENT DOCUMENTS 2414621  10/1975  Fed. Rep. of Germany.

OTHER PUBLICATIONS

Roberts et al., Basic Principles of Organic Chemistry, 1965, pp. 562–564.
Weygand/Hilgetag, Org. Chem. Experimentierkunst (1970), pp. 496–498.
Banci, J. Med. Chem. 14 (1971), 82/83.
Mutschler, Arzneimittelwirkungen, (1972), pp. 292–293.
Handbook of Chem. & Physics, 43rd ed. (1961), p. 752.

Primary Examiner—Henry R. Jiles
Assistant Examiner—Bernard Dentz
Attorney, Agent, or Firm—Stevens, Davis, Miller & Mosher

[57] ABSTRACT

Thiazolidine derivatives of formula

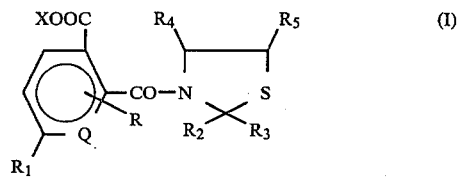

in which R, $R_1$, $R_2$, $R_3$, $R_4$ and $R_5$ have the meanings as defined in the specification, Q is CH or N and X is H or a pharmacologically acceptable cation derived from an inorganic or organic base limited to amino acids. These derivatives are obtained by condensing phthalic or quinolinic anhydride, possibly substituted in the ring, with the thiazolidine, optionally substituted, in an aprotic solvent. Said derivatives as well as the salts thereof possess a fluidizing mucosecretolytic action.

10 Claims, No Drawings

THIAZOLIDINE DERIVATIVES AND THEIR MUCOLYTIC COMPOSITIONS AND METHODS

This invention concerns thiazolidine derivatives and their salts with pharmacologically acceptable cations, having pharmacological activity. More specifically, the present invention relates to thiazolidine derivatives of formula

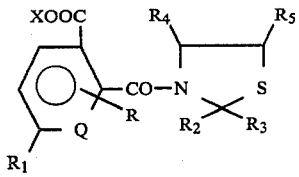

in which Q represents a methine group (≡CH) and wherein R and $R_1$, being the same or different, represent each a hydrogen atom, a halogen atom, a methyl, a hydroxy, an alkoxy or a nitro(—$NO_3$) group, or wherein Q represents a nitrogen atom, in which case $R=R_1=H$, and wherein in both cases $R_2$ and $R_3$, being the same or different, represent each a hydrogen atom, a ($C_1$-$C_4$) alkyl group, straight or branched, such as methyl, ethyl, propyl, t-butyl, a ($C_1$-$C_4$) alkenyl, such as, for example, vinyl, allyl, propenyl, crotyl; a cycloalkyl or cycloalkenyl group, having up to 5 carbon atoms in the ring, such as, for example, cyclopropyl, cyclobutyl, cyclopentyl, 2,2,3-trimethyl-cyclopenten-3-ylmethyl; aryl, such as, for example, phenyl, naphthyl, phenyl substituted with a hydroxyl group, a halogen atom, a ($C_1$-$C_4$) alkyl group, an amino group; a 5 to 6 numbered heterocyclic group such as, for example, thienyl, furyl, pyrrolidyl, imidazolyl, pyridyl, oxazolyl, thiazolyl, pyrimidinyl; $R_4$ and $R_5$, being same or different, represent each a hydrogen atom or a ($C_1$-$C_5$) alkyl group, and X represents a pharmacologically acceptable cation, as derived from an inorganic or organic base limited to any amino acid. In the context of this invention, the expression "pharmacologically acceptable cation as derived from an inorganic or organic base limited to an amino acid" stands for a cation derived from a hydroxide or an alkaline or earth-alkaline metal carbonate or from alpha- and beta-amino acids such as lysine and arginine.

This invention furthermore relates to a process for preparing the compounds of formula (I).

According to a presently preferred method, the thiazolidine derivatives of this invention are prepared by condensing either the phthalic anhydride (or the substitution derivatives thereof), or the quinolinic anhydride dissolved in an aprotic solvent, with the corresponding thiazolidine in base form, or salified with a hydrohalogenic acid, preferably hydrochloric acid.

In this latter case, a base must be added in a sufficient amount to neutralize the hydrochloric acid which develops during the reaction. The condensation may be carried out at a temperature between 15° C. and 80° C. in a period of 2 to 10 hours; at room temperature (15°-20° C.) with slight cooling, the condensation takes place in 8-10 hours; preferably, it is carried out at ca. 20°-60° C. and is generally completed in ca. 3-8 hours; still more preferably, it is carried out at 35° C.-40° C. in about 4-6 hours.

Obviously, as is known to those skilled in the art, the time required for condensation may vary not only according to the reaction temperature but also according to the reagents and solvents used. Examples of aprotic solvents useful for preparing the compounds of this invention are: methylene chloride, chloroform, benzene, cyclohexane. According to the solvents employed, also the temperature may vary and, consequently, the time of reaction. The temperature may rise up to 80° C. and the condensation time may be reduced to 2-3 hours.

The base useful for neutralizing the hydrohalogenic acid, which develops during the condensation reaction, obviously when a thiazolidine in salified form is used, is chosen amongst both inorganic and organic bases, with a marked preference for the former, since the use of organic bases entails an additional preparatory stage in the operations for purifying the finished product. Examples of useful inorganic bases are the hydroxides, bicarbonates and carbonates of the alkaline and earth-alkaline metals, with preference for sodium and potassium amongst the alkaline metals, for calcium amongst the earth-alkaline metals, with the exclusion of other metals of the same kind.

Among the organic bases, triethylamine is preferred.

The inorganic salts of formula (I) can be obtained by treating the acid of formula (I) in aqueous solution with the stoichiometric amount of a hydroxide, carbonate or bicarbonate corresponding to the desired inorganic salt. For example, by using a stoichiometric amount of sodium hydroxide, carbonate or bicarbonate, a solution of sodium salt of the acid of formula (I) is obtained. Upon elminitating the water by either evaporation or by addition of a solvent, both water-miscible and of moderate polarity such as, for example, a lower alkanol, a sodium inorganic salt is obtained.

The inorganic salts of amino acids deriving from formula (I), however, are obtained by reacting in water 1:1 stoichiometric amounts of the acids of formula (I) with amino acids (lysine) and evaporating to dryness, after filtering the aqueous solution.

The inorganic and organic salts of formula (I) are all water-soluble. The alkaline metal and calcium salts are obtained as infusible crystalline powder having a high rate of purity. From said salts, by cautious cold acidification with diluted hydrochloric acid, the corresponding acids are obtained. The acids of formula (I) may also be obtained directly from the reaction mixture, in which case they must be purified by crystallization according to the methods per se known.

The following Examples serve to better illustrate the preparation of the thiadolidine derivatives of formula (I) according to the process of the present invention. On the basis of the methodology as described in the following examples, those skilled in the art can easily prepare other thiazolidine derivatives falling within the scope of formula (I), not specifically exemplified or described, without any need for inventive contribution on their part.

EXAMPLE 1

2-(1,3-thiazolidin-3-yl)-carbonyl-benzoic acid (Na salt) (CO/1177)

$C_{11}H_{10}O_3NSNa$, M.W. 259.261.

In a laboratory reactor, provided with stirrer, thermometer, reflux condenser and dropping funnel, 148.12 g of pure phthalic anhydride is dissolved in 1500 ml of anhydrous methylene chloride, free from ethanol.

Under stirring, 89.16 g of pure thiazolidine base is added drop-wise over a period of 1-2 hours. The temperature rises slowly to 35° C. After the mixture has become homogenous and almost clear, it is kept under stirring for 3-4 hours. The end of the reaction is checked and then the following finishing treatment is carried out. The chloromethylene solution is first washed 2 times with 1 liter of water, then dehydrated, after separation with anhydrous $Na_2SO_4$, filtered and evaporated to dryness. The oily residue of impure acid product is taken up with an aqueous solution of 52 g of $Na_2CO_3$ in 500 ml of water. The alkaline solution is dry evaporated at reduced pressure. The dry residue is purified, by dissolving it in a 70% aqueous-alcoholic ethanol solution and, thereafter, by precipitating the pure sodium salt by addition of an equal volume of isopropanol.

Yield = 70% of the theory.

| Analysis: | Calculated | Found |
|---|---|---|
| For $C_{11}H_{10}O_3N\ S\ Na$ | C = 50.96 | C = 50.89 |
| | H = 3.89 | H = 3.87 |
| | N = 5.40 | N = 5.38 |
| | S = 12.37 | S = 12.33 |

I.R. spectrum (Mineral oil emulsion)
Characteristic bands ($cm^{-1}$)
1630 ($\gamma CO$ 1st amide band); 1605 ($\gamma_{as}$ COO$^-$); 1585 and 1555 ($\gamma C=C$ phenyl ring): 763 and 710. (as=asymmetric)

N.M.R. spectrum in $D_2O$
Reference standard DSS=Dimethylsilapentane Na sulphonate.
Characteristic AT signals ($\delta$p.p.m.)
8÷7.3 complex absorption (4H, aromatic nydrogens); 4.7s and 4.22s (2H, N—CH$_2$—S, rotation impeded around the amide bond C—N); 3.9t and 3.46t (2H,J=6.5 Hz, impeded rotation).

EXAMPLE 2

2-[(2-methyl)-1,3-thiazolidin-3-yl]-carbonyl-benzoic acid (Na salt) (CO/1218)

$C_{12}H_{12}O_3NSNa$ M.W. 273.291

Into a laboratory reactor, provided with a stirrer, thermometer and reflux condenser, are introduced 14.82 g of phthalic anhydride, 10.6 g anhydrous sodium carbonate F.U. (Italian Pharmacopoeia), 13.96 g of 2-methylthiazolidine.HCl in 150 ml of pure methylene chloride. The mixture is taken up to ebullition (40° C.) and is kept under stirring for 1-2 hours checking the end of the reaction. It is filtered, the solid product is taken up with 300 ml of chemically pure (C.P.) methanol, which dissolves the sodium salt of the product, leaving the inorganic salts undissolved. The methanol solution is evaporated to dryness, the raw product, free from any salts, is purified by following the method already described in Example 1, that is by precipitating the pure sodium salt with isopropanol from a hydroethanol solution.

Yield: 58% of the theory.

| Analysis: | Calculated | Found |
|---|---|---|
| For $C_{12}H_{12}O_3NSNa$ | C = 52.73 | C = 52.20 |
| | H = 4.43 | H = 4.35 |
| | N = 5.13 | N = 4.98 |
| | S = 11.73 | S = 11.58 |

I.R. spectrum (Mineral oil emulsion): characteristic bands ($cm^{-1}$)
1620 ($\gamma CO$, 1st amide band); 1600 ($\gamma_{as}$ COO$^-$); 1585 and 1560 ($\gamma C=C$, phenyl ring); 778 and 745.

N.M.R. spectrum in $D_2O$ (Reference standard DSS)
Characteristic AT signals ($\delta$p.p.m.)
8.1÷7.3 complex absorption (4H, aromatic hydrogens), 5.58 and 4.85q
(1H, NCHS, J=6.0 Hz, rotation impeded around the amide bond C—N)
1.47d and 1.21d (3H, CH—CH$_3$, J=6 Hz, impeded rotation)

EXAMPLE 3

2-[(2-ethyl)-1,3-thiazolidin-3-yl]-carbonyl-benzoic acid (Na salt) (CO/1217)

$C_{13}H_{14}O_3NSNa$ M.W. 287.311

Into a laboratory reactor, provided with a stirrer, thermometer, reflux condenser and dropping funnel, 150 ml of pure methylene chloride, 14.86 g of phthalic anhydride, 10.6 g of $Na_2CO_3$ F.U., 15.36 g of 2-ethylthiazolidine.HCl are introduced. The condensation reaction and the finishing treatment are carried out as in Example 2.

Yield = 60% of the theory.

| Analysis | Calculated | Found |
|---|---|---|
| For $C_{13}H_{14}O_3NSNa$ | C = 54.34 | C = 53.97 |
| | H = 4.91 | H = 4.75 |
| | N = 4.87 | N = 4.80 |
| | S = 11.16 | S = 11.00 |

I.R. spectrum (Mineral oil emulsion): characteristic bands ($cm^{-1}$)
1625 ($\gamma CO$, 1st amide band); 1602 ($\gamma_{as}$ COO$^-$); 1585 and 1560 ($\gamma C=C$, phenyl ring) 770 and 740.

N.M.R. spectrum in $D_2O$ (Reference standard DSS)
Characteristic AT signals ($\delta$p.p.m.)
8.1÷7.3 complex absorption (4H, aromatic hydrogens); 5.49dd and 4.99dd
(1H, N—CH—S, J=9 and 5 Hz, rotation impeded around the amide bond CN), 1.03t and 0.66t (3H, CH$_2$—CH$_3$, J=7.5 Hz, impeded rotation).

EXAMPLE 4

2-[(2-propyl)-1,3-thiazolidin-3-yl]-carbonyl-benzoic acid (Na salt) (CO/1226)

$C_{14}H_{16}O_3NSNa$, M.W. 301.341

The product is prepared similarly to that of Example 1 by reacting, in 150 ml of pure methylene chloride, 14.82 g of phthalic anhydride with 13.12 g of pure 2-propylthiazolidine base, and by completing the preparation by the same finishing and purifying methods of Example 1.

Yield = 45 of the theory.

| Analysis: | Calculated | Found |
|---|---|---|
| For $C_{14}H_{16}O_3NSNa$ | C = 55.80 | C = 55.70 |
| | H = 5.35 | H = 5.28 |
| | N = 4.65 | N = 4.80 |
| | S = 10.64 | S = 10.55 |

I.R. spectrum (Mineral oil emulsion); characteristic bands ($cm^{-1}$)

1633 (γCO, 1st amide band); 1610 (γ$_{as}$ COO⁻); 1590 and 1565 (γC=C, phenyl ring); 765 and 710.

N.M.R spectrum in D₂O (Reference standard DSS) Characteristic AT signals (δp.p.m.)

8.1÷7.3 complex absorption (4H aromatic hydrogens);

5.52dd and 4.73dd (1H, N—CH—S, J=9 and 5 Hz, rotation impeded around the amide bond CN); 0.98t and 0.51t (3H, CH₂—CH₂—CH₃, J=6.5 Hz, impeded rotation).

EXAMPLE 5

2-[(2-{2',2',3'-trimethyl-cyclopenten-3'yl}-methyl)-1,3-thiazolidin-3-yl]-carbonyl-benzoic acid, Na salt (CO/1178).

C₂₀H₂₄O₃NSNa M.W. 381.461

The product is prepared similarly to that of Example 1, by reacting, in 150 ml of pure methylene chloride, 14.82 g of phthalic anhydride with 21.67 g of pure 2(2',2',3'-trimethyl-cyclopenten-3'-yl)-methylthiazolidine base and completing the preparing by the same finishing and purifying method of Example 1.

Yield=45% of the theory.

| Analysis: | Calculated | Found |
|---|---|---|
| for C₂₀H₂₄N O₃S Na | C = 62.97 | C = 62.50 |
| | H = 6.34 | H = 6.22 |
| | N = 3.67 | N = 3.58 |
| | S = 8.41 | S = 8.32 |

I.R. spectrum (emulsion in mineral oil): characteristic bands (cm⁻¹)

1630 (γCO, 1st amide band) 1610 (γ$_{as}$ COO⁻); 1595 and 1670 (γC=C phenyl ring); 775 and 745.

N.M.R. spectrum in D₂O (reference standard DSS). Characteristic AT signals (δp.p.m.)

8.2÷7.0 complex absorption (4H, aromatic hydrogens)

1.55br s 1.40br s (CH=C—CH₃); 1.0s, 0.95s, 0.8s 0.77s, 0.65s and 0.57s (gem CH₃).

EXAMPLE 6

2-[(2-phenyl)-1,3-thiazolidin-3-yl]-carbonyl-benzoic acid (Na salt) (CO/1220)

C₁₇H₁₄O₃NSNa M.W. 335.351.

The product is prepared similarly to that of Example 1 by reacting, in 150 ml of pure methylene chloride, 14.8 g phthalic anhydride with 16.5 g of pure 2-phenyl-thiazolidine base and by completing the preparation by the same finishing and purifying method as that of Example 1.

Yield=68th of the theory.

| Analysis | Calculated | Found |
|---|---|---|
| for C₁₇H₁₄O₃N S Na | C = 60.88 | C = 60.76 |
| | H = 4.21 | H = 4.15 |
| | N = 4.18 | N = 4.12 |
| | S = 9.56 | S = 9.46 |

I.R. spectrum (emulsion in mineral oil): characteristic bands (cm⁻¹)

1625 (γCO, 1st amide band); 1608 (γ$_{as}$ COO⁻); 1585 and 1560 (γC=C phenyl ring); 760 and 705.

N.M.R. spectrum in D₂O (reference standard DSS). Characteristic AT signals (δp.p.m.)

8.1÷6.6 complex absorption (9H, aromatic hydrogens); 6.57s and 5.77s (1H, N—CH—S, rotation impeded around the amide bond C—N).

EXAMPLE 7

2-(1,3-thiazolidin-3-yl)-carbonyl-benzoic acid (CO/1177 bis)

C₁₁H₁₁NO₃S M.W. 237.274.

In a suitable reactor, provided with a stirrer, thermometer, reflux condenser, 29.6 g of phthalic anhydride is dissolved in 220 ml of pure anhydrous methylene chloride, free from ethanol; the mixture is reacted with 17.8 g of pure thiazolidine base, as in Example 1. When the reaction is completed, the chloro-methylene solution, washed two times with water, is dehydrated with anhydrous Na₂SO₄ and evaporated to dryness. The residue is crystallized from water, to give the pure acid product having m.p.=138° C.

| Analysis | Calculated | Found |
|---|---|---|
| for C₁₁H₁₁N O₃ S | C = 55.68 | C = 55.60 |
| | H = 4.67 | H = 4.64 |
| | N = 5.90 | N = 5.81 |
| | S = 13.51 | S = 13.46 |

I.R. spectrum (emulsion in mineral oil): characteristic bands (cm⁻¹)

1720 (γCO, acid); 1607 (γCO 1st amide band); 1590 and 1570 (γC=C phenyl ring); 775.

N.M.R. spectrum in CDCl₃ (reference standard, tetramethylsilane)

8.1÷7.2 complex absorption (4H aromatic hydrogens) 4.71s and 4.09s (2H, N—CH₂—S rotation impeded around the amide bond C—N) 3.98t and 3.39t (2H, J=6.5 Hz, impeded rotation, CONCH₂—CH₂) 3.04t and 2.88t (2H, J=6.5 Hz, impeded rotation CH₂—CH₂—S)

Mass spectrum Characteristic peaks, 70 eV 237(M+), 148; 104; 89; 76; 50

D.I.S. at 170° (Mass spectrometer model Hitachi RMU-6D)

EXAMPLE 8

2-(1,3-thiazolidin-3-yl)-carbonyl-benzoic acid (K salt) CO/1241

C₁₀H₁₀NO₃SK M.W. 275.364

In a laboratory reactor provided with a stirrer, reflux condenser, dropping funnel, 74.6 g of phthalic anhydride and 46.4 g of thiazolidine base, in 1000 ml pure anhydrous methylene chloride, free from ethanol, is reacted. The reaction is completed in an hour, the mixture is washed two times with distilled water and, after dehydration, the chloromethylene solution is evaporated to dryness under reduced pressure. The semisolid residue so obtained is taken up with an aqueous K₂CO₃ solution (32.6 g in 600 ml water). The solution is extracted repeatedly (3 times) with pure methylene chloride, and, after separation, is evaporated to dryness. A white crystalline mass is obtained, which is stove dried.

Yield=72% of theory.

| Analysis | Calculated | Found |
|---|---|---|
| for C₁₀H₁₀N O₃S K | C = 47.98 | C = 47.75 |
| | H = 3.66 | H = 3.58 |
| | N = 5.09 | N = 5.01 |

| Analysis | Calculated | Found |
|---|---|---|
|  | S = 11.64 | S = 11.58 |

The structure of the salt has been confirmed to agree with the I.R., N.M.R. structure (see Example 1).

EXAMPLE 9

2-(1,3-thiazolidin-3-yl)-carbonyl-benzoic acid (Ca salt) (CO/1240)

 M.W. 512.61

Note: 2 moles of o-Carbonyl-thiazolidine benzoic acid are salified by 1 atom of Ca.

One proceeds as in Example 8, by reacting 74.06 g of phthalic anhydride with 46.4 g of thiazolidine base, under identical conditions. The chloromethylene solution, after washing, is evaporated to dryness. The semi-solid residue is taken up with 500 ml water and, under strong stirring, is added 23.3 g of very pure $CaCO_3$ until pH is about 6.5. The excess $CaCO_3$ is filtered and the aqueous solution is washed repeatedly (3 times) with pure methylene chloride. The separated chloromethylene solution is evaporated to dryness, to give a white crystalline mass which is dried at 40° C., in a stove, under reduced pressure. Yield: 65% of the theory.

| Analysis | Calculated | Found |
|---|---|---|
| for $C_{22}H_{20}N_2O_6S_2Ca$ | C = 51.54 | C = 51.46 |
|  | H = 3.93 | H = 3.88 |
|  | N = 5.47 | N = 5.51 |
|  | S = 12.51 | S = 12.43 |

The structure of the salt has been confirmed to agree with the I.R., N.M.R. structure (see Example 1).

EXAMPLE 10

2-(1,3-thiazolidin-3-yl)-carbonyl-3-pyridine-carboxylic acid (Na salt) (CO/1242)

 M.W. 260.255

In a 500 ml reactor, provided with a stirrer, thermometer, reflux condenser, and dropping funnel, 14.9 g of quinoline anhydride (anhydride of 2,3-pyridine-dicarboxylic acid) is dissolved in 150 ml of pure methylene chloride, free from ethanol. In 1–2 hours, 8.9 g of pure thiazolidine base is added slowly, dropwise. The temperature rises from 20° to 25° C. and the mass becomes clear. It is stirred for 2–3 hours, checking the completion of the reaction. The mass is then evaporated to dryness. The semi-solid residue is taken up with a solution of 7.5 g of $NaHCO_3$ in 150 ml water, and evaporated to dryness. The dry sodium salt residue is hot treated with 180 ml of a hydroethanol solution (75% of ethanol) and precipitated with an equal volume of isopropanol.

Yield = 50% theory.

| Analysis | Calculated | Found |
|---|---|---|
| for $C_{10}H_9O_3N_2S\ Na$ | C = 46.15 | C = 45.95 |
|  | H = 3.49 | H = 3.40 |
|  | N = 10.77 | N = 10.82 |
|  | S = 12.32 | S = 12.11 |

I.R. spectrum (in mineral oil): characteristic bands $(cm^{-1})$ 1628 (γCO, 1st amide band); 1608 ($γ_{as}$ COO⁻); 1575 and 1557 (γC=C phenyl ring); 790 and 750.

N.M.R. spectrum in $D_2O$ (reference standard DSS) characteristic AT signals (δp.p.m.) 8.72dd, 840dd and 7.70dd (3H, aromatic protons); 4.79s and 4.28s (2H, N—$CH_2$—S), rotation impeded around the amide bond C—N) 4.00t and 3.53t (2H, J = 6 Hz, impeded rotation); 3.22t and 3.09t (2H, J = 6 Hz, impeded rotation).

The compounds of formula (I) are pharmacologically active. In particular, they show a remarkable fluidizing mucolytic activity, such as to make their employment especially desirable in human therapy in all cases of acute and chronic diseases of the respiratory apparatus, when associated with bronchial hypersecretion. Thus, this invention also relates to the pharmaceutical compositions which, in addition to suitable pharmaceutical vehicles, contain as an active substance a compound of formula (I) of the present invention.

In the context of the present specification, the term "pharmaceutical vehicle" refers to those pharmaceutically inert and non-toxic, solid or liquid, diluting or incapsulating, filling or carrying agents, which are usually employed in pharmaceutical industry for making pharmaceutical compositions. Some examples of substances which can be employed as pharmaceutical vehicles according to the various pharmaceutical forms are:

in the form of tablets-discoids, the preferred excipients are lactose, starch, (from maize or potato), cellulose or derivatives thereof, with all the additions which support the preparation of the pharmaceutical form, such as precipitated silica, talc, calcium or magnesium stearate.

In the form of suppositories, the main excipient consists of fatty acid triglycerides alone or mixed with oxyethylated derivatives of suitable molecular weight (polyethyleneglycols), products apt to preserve and keep stable the active compound, such as antioxidants, being optionally added; for the aerosol form, the powder forms are preferred, as obtained by mixing the active product with lactose or other inert powders.

For the preparation of injectable forms, the active compounds are taken in an isotonic solution to pH 7.5 and ampoule filling is effected under nitrogen, after cold sterilization; furthermore, the preparation of injectable lyophilized forms or in a sterile powder to be dissolved with an appropriate solvent phial may be employed.

In the form of granulates (sachets), the excipients employed are similar to those used in the form of tablets (sugars, starches, etc.).

Finally, in the syrup form, the active compounds are dissolved in aqueous sugar solutions (sucrose, glucose, etc.) possibly with the addition of sorbitol as well as coloring agents allowed by Law, aromatizing and preserving agents.

The compounds of formula (I) are administered either orally or parenterally by injection or as aerosol. The dosages of these compounds fall within 60 to 400 mg/day. More particularly, when in the tablet form: 2–4 tablets/day; in the syrup form: 1 measure twice a day up to the age of two years: over 2 years, 2 or more measures twice a day; in the form of phials: 1–2 phials/day; in the form of suppositories: 1–2 suppositories/day; in the form of aerosol: 1–2 applications/day.

The exact daily dose, however, depends of course on the age, body weight and conditions of the patient.

The present invention, furthermore, relates to the pharmaceutical compositions in unit dosages. This means that the pharmaceutical compositions are in the form of single portions, for example phials, tablets, discoids, capsules, suppositories, the contents of the active substance of which correspond to a fraction or a multiple of the single dose. The dosage units may, for example, contain either 1,2,3 or 4 single doses or ½, ⅓, ¼ of a single dose. A single dose contains, preferably, the amount of active substance which is administered in one application and which corresponds usually to the whole, one half, one third or one quarter of the daily dose. Preferred forms of the pharmaceutical compositions, in dosage units, are phials, tablets or discoids, aerosol in capsules or in solution, suppositories, syrups and sachets. More particularly, at present are preferred: Phials: 60 mg in 4 ml; Tablets or discoids: 100 g; Aerosol: 40 mg capsules or 1.5% solution; Suppositories: 200 mg; 100 mg; 20 mg; Syrup: 1%; Sachets: 100 mg. (The weights as indicated in mg as well as the quantities in percent denote the active substance contained).

EXAMPLES OF PHARMACEUTICAL COMPOSITIONS IN DOSAGE UNITS

For preparing the following pharmaceutical compositions, as a pharmacologically active substance has always been used the compound of Example 1, i.e. the sodium salt of o-carbonyl-thiazolidine benzoic acid, marked by the abbreviation CO/1177. This, mainly because said compound has shown the best characteristics. The preparation of the pharmaceutical compositions having, as pharmaceutical active substance, any other compounds of formula (I), does not present any difficulty for the skilled artisan; consequently, no limiting character of the present invention must be ascribed to the examples indicated here below:

| Example A: discoids | For 1 discoid |
|---|---|
| (1) o-Carbonylthiazolidine benzoic acid (Na salt) (CO/1177) | 100 mg |
| (2) Spray dried starch | 70 mg |
| (3) Spray dried lactose | 100 mg |
| (4) Microcrystalline cellulose | 70 mg |
| (5) Magnesium stearate | 5 mg |
| (6) Precipitated silica | 6 mg |
| (7) Talc | 6 mg |
| (8) Hydroxypropylmethylcellulose | 15 mg |
| (9) Titanium dioxide | 8 mg |

Preparation process

In an appropriate mixer are mixed the ingredients 1 to 7, the mixture is pressed on a rotary pressing machine and then the pellets are coated with a lacquer by dipping them into a solution of the ingredients 8 and 9 in a chlorinated solvent. Homogeneous discoids having a unit weight of 380 mg are thus obtained.

| Example B: Aerosol powder | For 1 capsule |
|---|---|
| (1) o-Carbonylthiazolidine benzoic acid (Na salt) (CO/1177) | 40 mg |
| (2) Lactose | 40 mg |

Preparation process

The two ingredients are mixed and the mixture is micronized to below 10 microns. The mixture is enclosed in hard gelatine capsules.

| Example C: Syrup | For 100 ml |
|---|---|
| (1) o-Carbonylthiazolidine benzoic acid (Na salt) (CO/1177) | 1 g |
| (2) 70% sorbitol | 30 g |
| (3) Saccharose | 20 g |
| (4) Glycerine | 5 g |
| (5) Fluid extract of bitter orange | 0.1 g |
| (6) Fluid extract of sweet orange | 0.2 g |
| (7) Deionized water q.s. to | 100 ml |

Preparation process

Into an AISI 304 stainless steel vessel, complete with stirrer, is placed a portion (1/5 of the total volume) of the deionized water and, under stirring, the ingredients 2,4,3,5,6-in that order-are added, while stirring to complete dissolution. The solution is taken to volume, it is filtered on a filter-press provided with small paperboard and hair-retaining filters and it is collected in an appropriate AISI 316 stainless steel container. The syrup is poured into yellow glass bottles dosed at 100 ml, which are closed using an aluminium cap with gasket.

| Example D: phials | For 1 phial |
|---|---|
| (1) o-Carbonylthiazolidine benzoic acid (Na salt) (CO/1177) | 60 mg |
| (2) Sorbitol | 100 mg |
| (3) Sodium metabisulfite | 1.5 mg |
| (4) Apyrogen bidistilled water q.s. to | 4 ml |

Preparation process

The solid ingredients 2,3,1 are dissolved, in that order, in apyrogenic bidistilled water (solution at ph 7.5), the solution is cold filtered under sterile condition and is filled into a dark phial under nitrogen. The so filled liquid is clear, colorless, sterile and apyrogenic.

| Example E: sachets of 5 g | For 1 sachet |
|---|---|
| (1) o-Carbonyl-thiazolidine benzoic acid (Na salt) (CO/1177) | 100 mg |
| (2) orange lyophilized | 750 mg |
| (3) Liquid glucose | 150 mg |
| (4) Orange essence | 40 mg |
| (5) Saccharose | 4060 mg |

Preparation process

A granular mixture is prepared with ingredients 2,3,4,5, comprising the active substance in the specified proportions. It is charged into thermosealable sachets at doses of 5 g/sachet.

| Example F: Suppositories | For 1 suppository |
|---|---|
| (1) o-Carbonylthiazolidine benzoic acid (Na salt) (CO/1177) | 200 mg |
| (2) Polyoxyethyleneglycole 1000 | 100 mg |
| (3) Polyoxyethyleneglycole 2000 | 100 mg |
| (4) 2-tert-butyl-4-hydroxyanisole | 10 mg |
| (5) Triglycerides of saturated fatty acids q.s. to | 2000 mg |

Preparation process

Into an appropriate AISI 304 stainless melter are poured the ingredients 5,2,3,4, melting the so obtained mass to about 37.5° C. and, under slow stirring, the micronized active substance is added, thus obtaining a homogeneous emulsion. The casting of the latter into containers, which are thermosealed and cooled, is performed. The m.p. of the suppositories is 37.5°–38° C.

Pharmacological assays

Here below are reported the results relating to the compound which presently is considered the most representative of the class, as defined by formula (I).

The pharmacological activity was measured by studying the effect on the compound (CO/1177) on:

(a) the mucus production by the rabbit according to the method described by R. Scuri and Coll.(Boll.Chim.-Farm.119, 181, 1980);

(b) viscosity of mucus of sound animals (rabbits) and/or of animals made bronchitic experimentally by using, for the viscosimeter measures, a Contraves Rehomat microviscosimeter at 15 automatic scanning speeds;

(c) "in vitro" viscosity of gastric mucin of the pig by using, for the viscometer measures, a Contraves Rehomat microviscosimeter at 15 automatic scanning speeds.

The acute and subacute toxicity tests were performed by using Swiss mice and Wistar rats of both sexes.

TABLE No. 1
Activity on mucus production of rabbit ($\bar{X} \pm$ E.S.)

| Substance | | Dose mg/kg | Admin. route | Mucroproduction: mg/h at hours −4 | 0 | 0 | −4 | Var. % |
|---|---|---|---|---|---|---|---|---|
| Controls | (8) | — | os | 17.880 ± 6.250 | | 16.910 ± 8.320 | | −5.5 |
| CO/1177 ≠ | (10) | 400 | os | 15.550 ± 5.040 | | 30.730 ± 7.630** | | +97.6 |
| | (7) | 200 | os | 57.030 ± 5.580 | | 86.250 ± 10.80** | | +51.2 |
| | (10) | 100 | os | 29.490 ± 5.330 | | 34.320 ± 5.850 | | +16.3 |
| Controls | (10) | — | os | 21.818 ± 1.095 | | 23.003 ± 0.951 | | +5.4 |
| N—Acetylcysteine | (10) | 600 | os | 23.308 ± 1.071 | | 32.512 ± 1.365** | | +39.4 |
| | | 400 | os | 21.685 ± 0.791 | | 22.713 ± 0.947 | | +4.7 |
| S—Carboxymethyl-cysteine | (10) | 600 | os | 23.923 ± 1.247 | | 32.120 ± 1.630** | | +34.2 |
| | | 400 | os | 26.925 ± 1.143 | | 35.339 ± 1.376** | | +31.2 |
| Mercaptopropionyl-glycine | (10) | 600 | os | 22.958 ± 1.213 | | 34.432 ± 1.813** | | +49.9 |
| | | 400 | os | 22.097 ± 0.964 | | 32.053 ± 1.292** | | +45.0 |
| Bromexine | (10) | 600 | os | 24.483 ± 1.087 | | 34.440 ± 1.446** | | +40.6 |
| | | 400 | os | 20.866 ± 0.768 | | 27.414 ± 1.071** | | +31.3 |
| Controls | (9) | — | i.v. | 20.380 ± 8.250 | | 18.550 ± 7.830 | | −8.0 |
| CO/1177 ≠ | (10) | 10 | i.v. | 28.790 ± 4.750 | | 49.250 ± 6.020** | | +71.0 |
| | (10) | 5 | i.v. | 27.950 ± 1.032 | | 37.650 ± 0.231** | | +34.6 |
| | (10) | 2.5 | i.v. | 39.690 ± 1.688 | | 52.760 ± 20.29** | | +32.0 |
| Controls | (10) | — | i.v. | 21.202 ± 0.838 | | 21.099 ± 0.606 | | −0.5 |
| N—Acetylcysteine | (10) | 10 | i.v. | 20.678 ± 0.624 | | 30.988 ± 1.078** | | +49.8 |
| | | 5 | i.v. | 22.478 ± 0.740 | | 29.058 ± 0.946** | | +29.2 |
| Mercaptoproprionyl-glycine | (10) | 20 | i.v. | 25.615 ± 1.108 | | 36.630 ± 1.565** | | +43.0 |
| | | 10 | i.v. | 23.990 ± 1.043 | | 32.121 ± 1.013** | | +33.8 |
| Controls | (9) | — | i.v. | 20.380 ± 8.250 | | 18.550 ± 7.830 | | −8.0 |
| CO/1220 ≠ | (8) | 10 | i.v. | 21.740 ± 3.810 | | 31.300 ± 2.240** | | +43.5 |
| CO/1226 ≠ | (8) | 10 | i.v. | 23.410 ± 2.710 | | 29.730 ± 4.510 | | +26.9 |
| CO/1178 ≠ | (7) | 10 | i.v. | 22.410 ± 4.710 | | 26.890 ± 6.210 | | +19.9 |
| CO/1242 ≠ | (8) | 10 | i.v. | 23.510 ± 3.810 | | 31.030 ± 2.840* | | +39.0 |

**$P < 0.01$
*$P < 0.05$
E.S. = meaningful error
( ) Number of animals
≠ Examples of the series terms as mentioned and endowed with pharmacological activity

| | Dose | | Fluidizing activity - Sound animals - Administration by intravenous route Viscosity: cps at the speeds - g/min. ($\bar{X}$) | | | | | | | | | | |
|---|---|---|---|---|---|---|---|---|---|---|---|---|
| Sostanza | mg/Kg | Tempo | 17.4 | 25 | 33.6 | 44.3 | 56.1 | 77.9 | 113.2 | 152 | 200 | 266.8 | 352 |
| Controlli (4) | — | −24→0 | 10.15 | 9.85 | 9.00 | 8.00 | 7.50 | 5.20 | 4.10 | 3.70 | 3.31 | 3.20 | 3.00 |
| | | 0–24 | 12.50 | 10.70 | 8.50 | 7.00 | 6.80 | 6.00 | 5.20 | 4.00 | 3.80 | 3.40 | 3.20 |
| Var. % | | | +23 | +8.6 | +5.6 | −12.5 | −9.4 | +15 | +36 | +8 | +14 | +6 | +6 |
| CO/1177 (4) | 20 | −24→0 | 9.56 | 10.58 | 9.20 | 7.00 | 7.50 | 5.49 | 3.61 | 3.42 | 3.48 | 3.19 | 3.05 |
| | | 0–24 | 0 | 0.88 | 1.97 | 2.00 | 2.43 | 2.55 | 2.25 | 2.18 | 2.04 | 1.94 | 1.91 |
| Var. % | | | −100 | −81.7 | −78.6 | −71.5 | −67.6 | −53.6 | −37.7 | −36.3 | −41.4 | −39.2 | −37.4 |

( ) Numero animali

TABLE No. 3

| | Dose | | Fluidizing activity - bronchitic animals - Intravenous administration Viscosity: cps. at the speeds - g/min. ($\bar{X}$) | | | | | | | | | | |
|---|---|---|---|---|---|---|---|---|---|---|---|---|
| Substance | mg/Kg | Time | 17.4 | 25 | 33.6 | 44.3 | 56.1 | 77.9 | 113.2 | 152 | 200 | 266.8 | 352 |
| Controls (4) | — | −24–0 | 138.47 | 100.7 | 82.67 | 69.2 | 38.57 | 24.4 | 20.4 | 15.5 | 11.4 | 8.0 | 5.8 |
| | | 0–24 | 141.50 | 110.2 | 91.40 | 75.2 | 44.60 | 28.7 | 25.2 | 18.0 | 13.4 | 10.3 | 6.2 |
| Var. % | | | +2 | +9 | +10 | +17 | +15 | +17 | +23 | +16 | +27 | +28 | +6 |
| CO/1177 (4) | 20 | −24–0 | 149.30 | 99.7 | 71.70 | 51.6 | 30.10 | 27.4 | 18.5 | 16.3 | 12.0 | 8.5 | 6.0 |
| | | 0–24 | 50.30 | 41.5 | 28.70 | 22.4 | 14.50 | 10.7 | 6.7 | 5.2 | 4.0 | 2.4 | 1.9 |
| Var. % | | | −66.4 | −58.4 | −60 | −56.6 | −51.9 | −60.9 | −63.8 | −68.1 | −66.7 | −71.8 | −68.9 |

( ) Number of animals

TABLE No. 4

| Substance | Conc. % | Fluidizing activity "in vitro" - Gastric mucin of pig Viscosity: cps. at the speed - g/min. ($\bar{X}$) | | | | | | | | | |
|---|---|---|---|---|---|---|---|---|---|---|---|
| | | 17.4 | 25 | 33.6 | 44.3 | 56.1 | 77.9 | 113.2 | 152 | 200 | 266.8 | 352 |
| Mucin + H$_2$O (0.1 ml) | — | 27.66 | 27.65 | 26.73 | 26.66 | 26.00 | 24.61 | 22.70 | 20.69 | 18.74 | 17.20 | 15.37 |
| CO/1177 | 2 | 24.87 | 22.39 | 24.05 | 22.92 | 23.14 | 20.91 | 20.88 | 18.81 | 17.24 | 15.48 | 14.29 |
| Var. % | | −10.9 | −19.1 | −10.1 | −14.1 | −11 | −15.4 | −8.1 | −9.1 | −8.1 | −10 | −7.1 |
| Mucin + H$_2$O (0.1 ml) | — | 28.81 | 27.40 | 27.00 | 26.51 | 25.84 | 22.81 | 21.57 | 19.50 | 18.20 | 16.51 | 14.90 |
| N—Acetylcysteine | 2 | 25.64 | 25.20 | 24.30 | 23.32 | 23.77 | 20.30 | 19.41 | 17.94 | 16.19 | 14.52 | 13.70 |
| Var. % | | −11.9 | −8.1 | −10 | −12.4 | −8.1 | −11.1 | −10.1 | −8 | −11.1 | −12.1 | −8.1 |

TABLE No. 5

| | Acute toxicity | | |
|---|---|---|---|
| Substance CO/1177 | Animal species | Administration route | LD$_{50}$-mg/kg |
| | Mouse | i.v. | 3000 |
| | | os | >5000 |
| | Rat | i.v. | >5000 |
| | | os | >5000 |
| | Rabbit | i.v. | ~3500 |

Subacute toxicity

Wistar rats of both sexes and in groups of 20 units/sex/dose were used. The duration of the treatment was 4 weeks and the administration routes were the oral (gastric tube) and the subcutaneous route.

The following parameters were recorded: general behaviour, mortality, food consumption, weight growth, hematologic tests, hematochemical tests, urine tests, weight and histologic tests of the most important organs.

The doses employed were: 150-300-1200 mg/kg per os and 150-300-900 mg/kg s.c.

The compound according to this invention, CO/1177, showed toxic effects only at the dose of 1200 mg/kg os.

I claim:
1. A compound of the formula

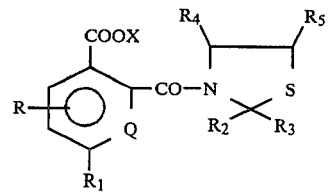

wherein Q is —CH= or N=, R and R$_1$ are hydrogen, R$_2$ and R$_3$, which can differ from each other, each represents a hydrogen atom, (C$_1$-C$_4$)-alkyl group, straight or branched, (C$_2$-C$_4$)-alkenyl, a phenyl or a 2,2,3-trimethyl-cyclopenten-3-ylmethyl group, a thienyl, furyl, pyrrolidyl, imidazolyl, pyridyl, oxazolyl, thiazolyl or pyrimidinyl moiety, and R$_4$ and R$_5$ are hydrogen and X represents a pharmacologically acceptable cation deriving from an inorganic base or a basic amino acid.

2. 2-(1,3-thiazolidin-3-yl)-carbonyl-benzoic acid sodium salt.

3. 2-[(2-propyl)-1,3-thiazolidin-3-yl]-carbonyl-benzoic acid sodium salt.

4. 2-[(2-phenyl)-1,3-thiazolidin-3-yl]-carbonyl-benzoic acid sodium salt.

5. 2-[2-{2',2',3'-trimethyl-cyclopenten-3'-yl}-methyl)-1,3-thiazolidin-3-yl]-carbonyl-benzoic acid sodium salt.

6. 2-(1,3-thiazolidin-3-yl)-carbonyl-benzoic acid sodium salt.

7. 2-(1,3-thiazolidin-3-yl)-carbonyl-3-pyridine-carboxylic acid sodium salt.

8. A mucolytic fluidifying pharmaceutical composition characterized in that it comprises a pharmacologically effective amount of a compound of formula (I), according to claim 1, as an active ingredient, in combination with at least a pharmaceutical vehicle.

9. A mucolytic pharmaceutical composition characterized in that it comprises, as an active ingredient, a pharmaceutically effective amount of any one of the compounds of claims 2-7, in combination with at least a pharmaceutical vehicle.

10. A mucolytic pharmaceutical composition characterized in that it comprises from 20 mg to 400 mg of a compound of formula (I), according to claim 1, as an active ingredient, and at least a pharmaceutical vehicle in the unit dosage form.

* * * * *